United States Patent [19]

Bannard et al.

[11] Patent Number: 5,117,116

[45] Date of Patent: May 26, 1992

[54] METHOD AND DEVICE FOR MONITORING UV RADIATION

[75] Inventors: John E. Bannard; Dennis D. Maguire, both of Nottingham, England

[73] Assignee: Cybrandian Limited, Limerick, Ireland

[21] Appl. No.: 624,748

[22] Filed: Dec. 11, 1990

[30] Foreign Application Priority Data

Dec. 11, 1989 [IE] Ireland .................................. 3945/89

[51] Int. Cl.$^5$ .............................................. G01J 1/50
[52] U.S. Cl. .................................. 250/474.1; 250/472.1
[58] Field of Search .................. 250/474.1, 372, 472.1

[56] References Cited

U.S. PATENT DOCUMENTS

| | | | |
|---|---|---|---|
| 3,194,963 | 7/1965 | McKee | 250/474.1 |
| 3,449,572 | 6/1989 | Sylvester et al. | 250/474.1 |
| 3,903,423 | 9/1975 | Zweig | 250/474.1 |
| 4,818,491 | 4/1989 | Fariss | 250/372 |

Primary Examiner—Carolyn E. Fields
Attorney, Agent, or Firm—Laubscher, Presta & Laubscher

[57] ABSTRACT

A device for monitoring UV radiation received by the skin comprises a housing. Adhesive on a face of the housing secures the device to the skin. A patch of irreversible UV sensitive material which changes color on being subjected to UV radiation is applied to an inner surface of the housing and receives UV radiation reflected from the skin. The color of the UV sensitive patch is compared with reference colors on the housing for determining the quantity of UV radiation to which the skin has been subjected.

20 Claims, 3 Drawing Sheets

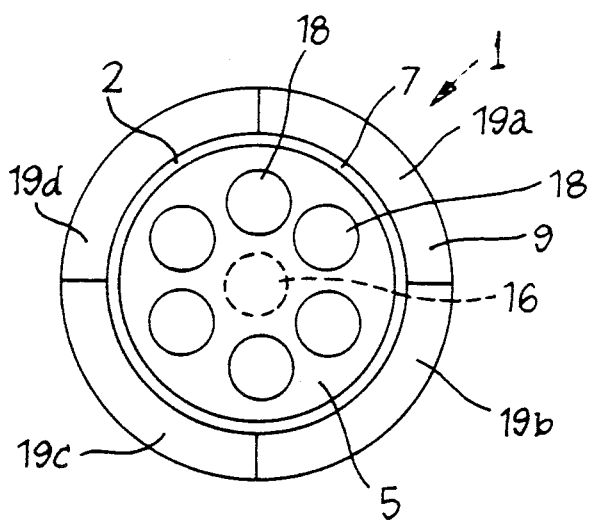
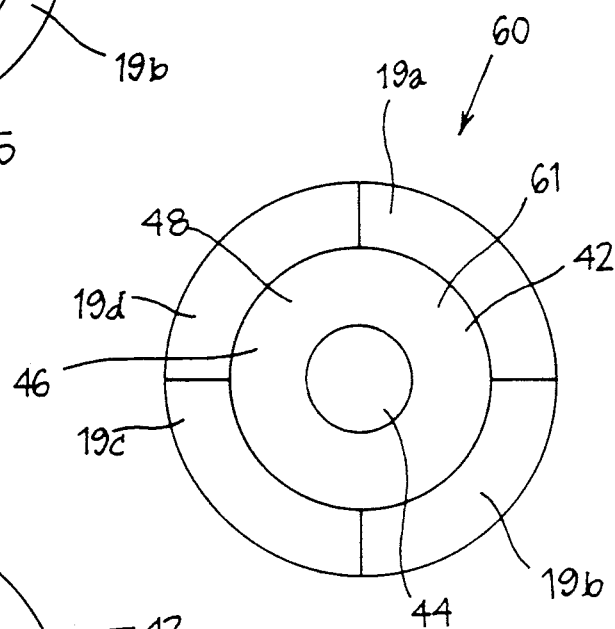
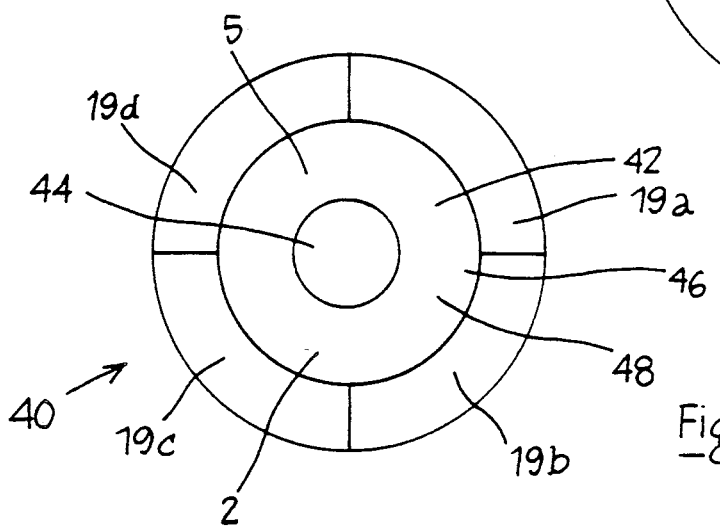
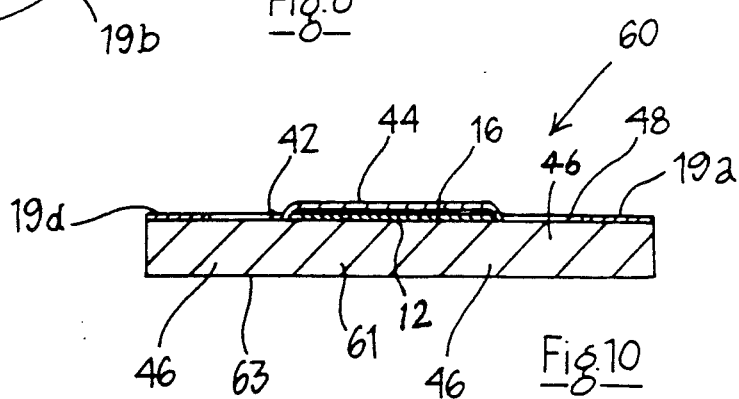

METHOD AND DEVICE FOR MONITORING UV RADIATION

FIELD OF THE INVENTION

The present invention relates to a method and device for monitoring the quantity of ultra-violet radiation, hereinafter referred to as "UV radiation" received by the skin of an individual.

BACKGROUND TO THE INVENTION

It has been known for some time that over-exposure of the skin to UV radiation can result in damage to the skin which varies in severity from slight reddening and accompanying soreness to severe burning. Further, over-exposure to UV radiation, especially to the shorter wavelengths of UV radiation, namely 280 nanometers to 320 nanometers, it is believed can lead to the development of skin cancer, especially melanoma. The risk of one developing skin cancer or other complications depends on the quantity of UV radiation to which the skin is subjected. It has also been found that people whose skin pigmentation is relatively light in colour, in other words, fair-skinned people, tend to have less tolerance to UV radiation than those of darker skin The skin reacts to radiation by changes in the melanin content. However, prior to a change in the melamine content, reddening occurs and then subsequently soreness and burning ensue. To facilitate quantifying the minimum dose of UV radiation an individual can tolerate, the dose of UV radiation which induces reddening in the skin is referred to as the Minimum Erythemal Dose, hereinafter referred to as MED. A fair-skinned person, in general, can tolerate approximately one MED, while a rugged skinned person with well tanned skin who rarely burns could tolerate up to twelve MED3 s or more. An individual would normally be subjected to one MED of UV radiation in equatorial regions at midday in approximately ten to fifteen minutes.

It is believed that the active component of the UV radiation is the UVB element of the spectrum. Specifically, the element of the spectrum of wavelength of the order of 280 nanometers to 320 nanometers.

Devices for monitoring the quantity of UV radiation received by the skin, in general, are referred to as sun dosimeters. Usually, dosimeters comprise a support member and a photochromic material which is sensitive to UV light of wavelength in the range of 280 to 320 nanometers. A plurality of reference colours or shades are provided round the photochromic material. The reference colours correspond to the colour or shade the photochromic material would achieve after being subjected to respective specific doses of UV radiation. These devices, in general, are placed adjacent or on a sunbather, and exposed to the sun while the individual's skin is similarly exposed. Periodically, the individual can check the colour or shade of the photochromic material against the reference colour to establish the dose of UV radiation to which the device and skin have been exposed. However, while these devices are adequate for an individual sunbathing for a single uninterrupted period per day, they are inaccurate for use where the individual sunbathes for a number of periods each day. The reason for this is that the photochromic materials are reversible materials. In other words, when the photochromic material is no longer exposed to UV radiation, the material begins to revert to its original colour or shade. Depending on the photochromic material used, this reversal procedure may be fast or slow. Clearly, the faster the reversal procedure, the less effective these devices are, since the effect on the skin of UV radiation is cumulative over a day. Accordingly, where an individual takes a number of breaks from sunbathing during a day and the dosimeter is unexposed to the sun during the periods of the breaks, the dosimeter commences to reverse o being removed from the UV radiation There is therefore a need for a method and device for monitoring the quantity of UV radiation to which an individual's skin is subjected which overcomes the problems of known methods and devices.

OBJECT OF THE INVENTION

One object of the invention is to provide a method and device which permits the dose of UV radiation to which the skin is subjected to be monitored relatively accurately. Another object of the invention is to provide a method and device which permits the dose of UV radiation to which the skin is subjected to be determined relatively accurately. Another object of the invention is to provide a method and device which permits the dose of UV radiation to which the skin is subjected to be monitored relatively accurately even in cases where the skin of the individual is periodically exposed to UV radiation over a period of a day, and in the intervening periods between the periods of exposure, the individual's skin is protected from the UV radiation. A further object of the invention is to provide a device for monitoring and determining the dose of UV radiation to which the skin of an individual is subjected, which is relatively cheap to produce. A further object is to provide such a device which is relatively easy to produce and is also relatively easy to use.

SUMMARY OF THE INVENTION

According to the invention, there is provided a device for monitoring the quantity of UV radiation received by the skin, the device comprising a support means defining a support surface, a substantially irreversible UV sensitive material on the support surface, the UV sensitive material having a characteristic which alters substantially irreversibly on being subjected to UV radiation, securing means for attaching the support means to the skin with at least portion of the UV sensitive material spaced apart from the skin to receive reflected UV radiation from the skin.

In one embodiment of the invention, filter means is provided to prevent at least some UV radiation direct from the UV radiation source falling on the UV sensitive material.

In another embodiment of the invention, the filter means acts as a barrier to UV radiation of wavelength in the range of 260 nanometers to 400 nanometers.

Preferably, the filter means is transparent to allow the UV sensitive material to be viewed therethrough.

In another embodiment of the invention, at least one reference characteristic is provided for comparison with the UV sensitive material, the reference characteristic corresponding to the state to which the characteristic of the UV sensitive material would alter after the UV sensitive material had been subjected to a predetermined quantity of UV radiation. Preferably, the reference characteristic is provided in a plurality of different reference states, the reference states corresponding to respective states to which the characteristic of the UV sensitive material would alter after the UV sensitive material had been subjected to respective different predetermined quantities of UV radiation In one embodiment of the invention, the characteristic of the UV sensitive material which alters is the colour of the UV sensitive material, the reference characteristic being a plurality of different colours.

In another embodiment of the invention, the characteristic of the UV sensitive material which alters is the optical density of colour of the UV sensitive material, the reference characteristic comprising a plurality of different shades of the colour.

In another embodiment of the invention, the support member forms the filter means. Advantageously, window means is provided in the support means to permit the passage of UV radiation therethrough to the skin.

In a further embodiment of the invention, the UV sensitive material is selected from any one or more of the following materials:

oxazolidine-dione compounds such as the type disclosed in U.S. Pat. No. 3,903,423, xanthenone compounds of the type disclosed in U.S. Pat. No. 3,903,423, tetrazolium salts of the type disclosed in U.S. Pat. No. 3,449,572, 2(2'4' dinitrobenzyl)pyridine referred to in U.S. Pat. No. 3,194,963 photosensitive onium salts in the presence of a dyestuff which changes colour when protonated of the type disclosed in U.S. Pat. No. 4,659,649 and any other photosensitive system that can be used to produce a colour or a colour change.

Additionally, the invention provides a method for monitoring the quantity of UV radiation received by the skin, the method comprising the step of placing an irreversible UV sensitive material adjacent the skin of an individual, the UV sensitive material having a characteristic which alters on being subjected to UV radiation, collecting UV radiation reflected by the skin in the UV sensitive material, observing the UV sensitive material to determine a change in the characteristic in the UV sensitive material for determining the quantity of UV radiation received by the skin.

Preferably, the method further comprises the step of comparing the characteristic of the UV sensitive material with a reference characteristic, the reference characteristic corresponding to the state to which the characteristic of the UV sensitive material would alter after the UV sensitive material had been subjected to a predetermined quantity of UV radiation.

ADVANTAGES OF THE INVENTION

The advantages of the invention are many. One of the main advantages of the invention is that the dose of UV radiation to which an individual's skin has been subjected can readily easily and accurately be monitored. Another advantage of the invention is that the device according to the invention is relatively inexpensive and easy to produce. A further advantage of the invention is that the device according to the invention is relatively easily used.

These advantages and objects will be readily apparent to those skilled in the art from the following description of some preferred embodiments thereof, which are given by way of non-limiting example with reference to the accompanying drawings.

BRIEF DESCRIPTION OF THE DRAWINGS

FIG. 3 is a partly cut away perspective view of the device of FIG. 1 from a different direction, FIG. 4 is a top plan view of the device of FIG. 1, FIG. 6 is a perspective view of a device according to a further embodiment of the invention, FIG. 8 is a top plan view of the device of FIG. 6, FIG. 9 is a cross-sectional view of a device according to another embodiment of the invention, FIG. 10 is a cross-sectional view of a device according to a still further embodiment of the invention, and FIG. 11 is a plan view of the device of FIG. 10.

DETAILED DESCRIPTION OF THE INVENTION

Figure 1:
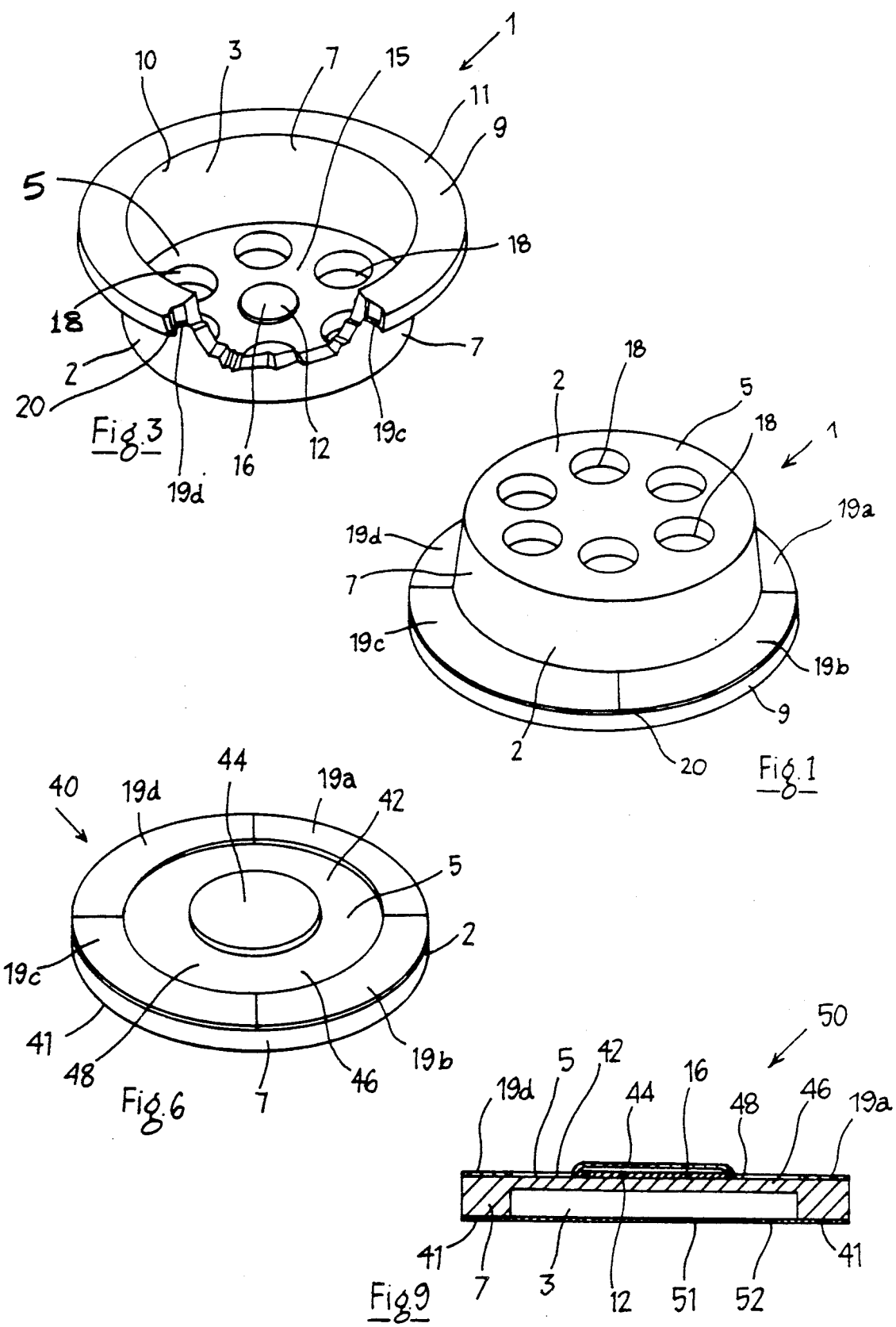
FIG. 1 is a perspective view of a device according to the invention for monitoring the UV radiation received by the skin.
Figure 2:
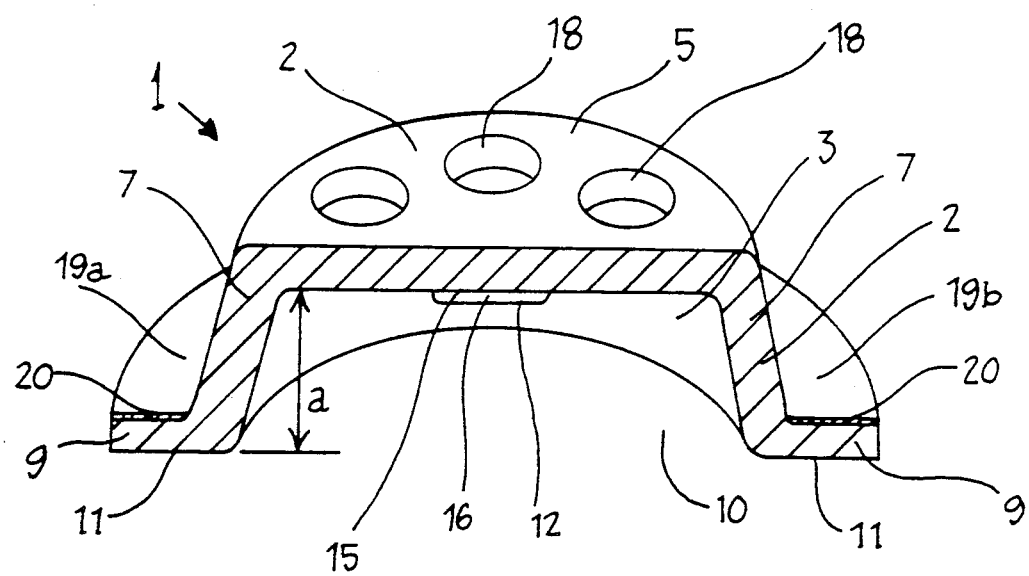
FIG. 2 is a cut-away perspective view of the device of FIG. 1.

Referring to the drawings, and initially to FIGS. 1 to 4, there is illustrated a device according to the invention indicated generally by the reference numeral 1 for monitoring the quantity of UV radiation received by the skin of an individual. The device 1 measures the cumulative UV radiation which has been reflected from the skin of the individual. The device 1 comprises a housing 2 of transparent plastics material, in this case polyvinyl chloride which is stabilised against degradation by UV radiation of wavelengths up to 320 nanometers. The housing 2 defines a hollow interior region 3 and is formed by a circular top wall 5 and a side wall 7 extending around the top wall 3 and downwardly therefrom. The side wall 7 defines a circular open mouth 10 to the hollow interior region 3. A flange 9 extends outwardly around the side wall 7 adjacent the open mouth 10. Securing means for securing the housing 2 to the skin of an individual with the open mouth 10 adjacent the skin comprises a pressure sensitive adhesive on a face 11 of the flange 9. The top wall 5 forms a support means in the form of a plate member for supporting an irreversible UV sensitive material 12 spaced apart from the individual's skin for receiving reflected UV radiation from the individual's skin. A circular patch 16 of the irreversible UV sensitive material 12 is applied substantially centrally on an inner support surface 15 of the top wall 5. The patch 16 is painted on to the support surface 15. In this embodiment of the invention, the height a of the side wall 7 is 3 mm from the inner support surface 15. Accordingly, the patch 16 is supported at a distance of approximately 3 mm from the skin of the individual.

In this embodiment of the invention, the irreversible UV sensitive material 12 is an oxazolidine-dione compound and is sensitive to UV radiation of wavelength in the range of 280 nanometers to 320 nanometers. A characteristic of the UV sensitive material 12, which in this case is the colour of the material, alters on the patch 16 being subjected to UV radiation and the colour to which the patch 16 alters is a function of the quantity of UV radiation of wavelength in the range of 280 nanometers to 320 nanometers to which the patch 16 is subjected. The housing 2, and in turn the top wall 5 being of polyvinyl chloride material stabilised against UV radiation of wavelength up to 320 nanometers acts as a filter means to filter out UV radiation, and thus acts as a bar to UV radiation of wavelength in the range of 280 nanometers to 320 nanometers. Accordingly, although the housing 2 is transparent allowing the patch 16 to be viewed, the patch 16 of UV sensitive material 12 is protected from direct UV radiation from the source, in general which would be the sun, and only UV radiation reflected from the skin is received and absorbed by the patch 16

Window means comprising a plurality of window openings 18 extending through the top wall 5 accommodate the passage of UV radiation through the top wall 5 onto the individual's skin in the area of the open mouth 10. The total area of the openings 18 constitutes approximately 50% of the area of the top wall 5. Four reference characteristics comprise reference patches 19a to 19d of different reference colours on a face 20 of the flange 9 around the side wall 7 for enabling an individual to detect the quantity of UV radiation to which the individual's skin has been exposed. The patches 19 are provided by suitable dyes or paints which are painted on to surface 20. The reference colours 19a to 19d correspond to respective colours to which the patch 16 of UV sensitive material 12 alters on being subjected to respective different predetermined quantities of UV radiation of wavelength in the range of 280 nanometers to 320 nanometers. In this embodiment of the invention, the colour of the patch 19a corresponds to an exposure to UV radiation equivalent to one MED. The colour of the patch 19b corresponds to an exposure to UV radiation equivalent to two to three MED's. The colour of the patch 19c corresponds to an exposure of UV radiation equivalent to three to six MED's, while the colour of the patch 19d corresponds to an exposure to UV radiation of six to ten MED's. The reference patches 19a to d are arranged around the side wall 7 so that an individual can simultaneously view the reference colours 19a to d on viewing the patch 16 of UV sensitive material 12 through the top wall 5 to facilitate ease of comparison of the colour of the patch 16 with the reference colours 19a to d, thereby enabling an individual to determine their level of exposure to UV radiation.

In use, the device 1 is attached to the skin of an individual by pressing the housing 2 against the skin of the individual with the face 11 of the flange 9 abutting the individual's skin to cause the pressure sensitive adhesive to bond the flange 9 to the individual's skin. The device 1 may be attached to the arm, back, chest or indeed any other suitable part of the individual's body which is being exposed to UV radiation, for example sunlight. The patch 16 receives UV radiation reflected from the individual's skin. As the quantity of reflected UV radiation received by the patch 16 increases, the colour of the patch 16 varies sequentially through the colours 19a to d. An individual, by periodically checking the colour of the patch 16 against the reference colours 19a to d can readily easily determine their cumulative exposure to UV radiation. Should an individual wish to cease sunbathing for a short period, the device 1 may be left on the skin of the wearer if the wearer so wishes. By virtue of the fact that the UV sensitive material 12 of the patch 16 is irreversible, the colour to which the patch has changed remains unaltered during the period while the device is not exposed to UV radiation. On recommencing sunbathing, the individual again exposes the portion of the body, to which the device 1 has been attached, to the UV radiation. As the patch 16 is further subjected to reflected radiation from the skin, the colour of the patch continues to alter to the next reference colour sequentially. The device 1 shows the cumulative quantity of UV radiation to which the skin has been exposed.

An individual, on knowing his or her tolerance level, namely the MED number to which they can tolerate UV radiation, can readily easily determine when they have received sufficient radiation. An individual will have received sufficient radiation when the colour of the patch 16 corresponds to the reference colour 19a to d corresponding to the MED tolerance level the individual can tolerate.

Needless to say, when an individual has ceased sunbathing for a sufficient period of time to allow the skin to recover, it is necessary to use a new device 1 for the next sunbathing session.

Figure 5:
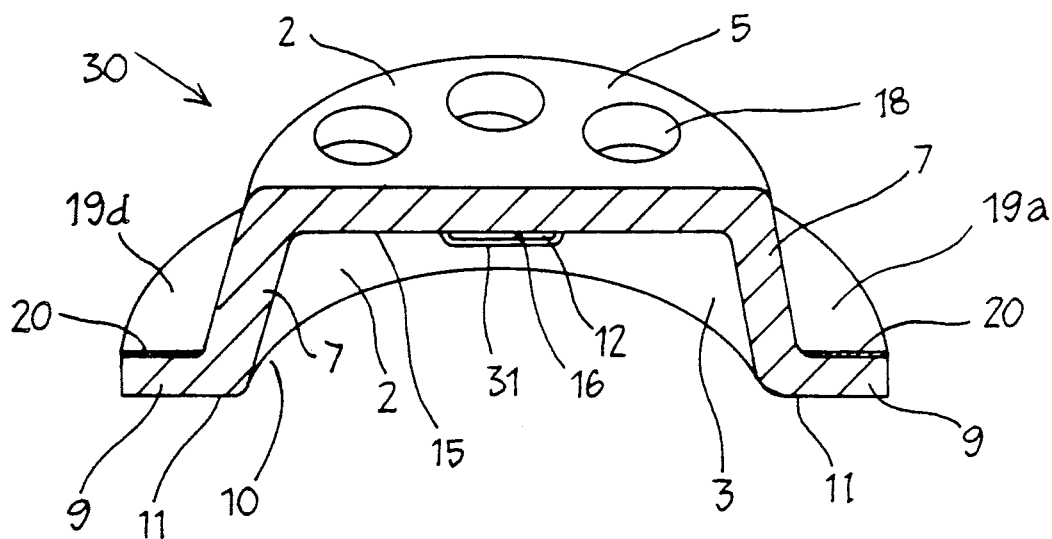
FIG. 5 is a cut-away perspective view similar to FIG. 2 of a device according to another embodiment of the invention.

Referring now to FIG. 5, there is illustrated a device according to another embodiment of the invention indicated generally by the reference numeral 30 for monitoring the quantity of UV radiation received by the skin. The device 30 is substantially similar to the device 1 described with reference to FIGS. 1 to 4, and similar components are identified by the same reference numerals. The main difference between the device 30 and the device 1 is that a protective layer or screen 31 is provided over the patch 16 of irreversible UV sensitive material 12. The protective layer 31 protects the patch 16 prior to use. The protective layer 31 is of a UV sensitive material selected from a range of diazonium materials which breaks down rapidly on being subjected to UV radiation. Accordingly, within minutes of the device 1 being exposed to UV radiation, the protective layer 31 breaks down, thereby exposing the patch 16 to the full effects of the UV radiation reflected from the skin. Use of the device 31 is similar to use of the device 1 described with reference to FIGS. 1 to 4.

Figure 7:
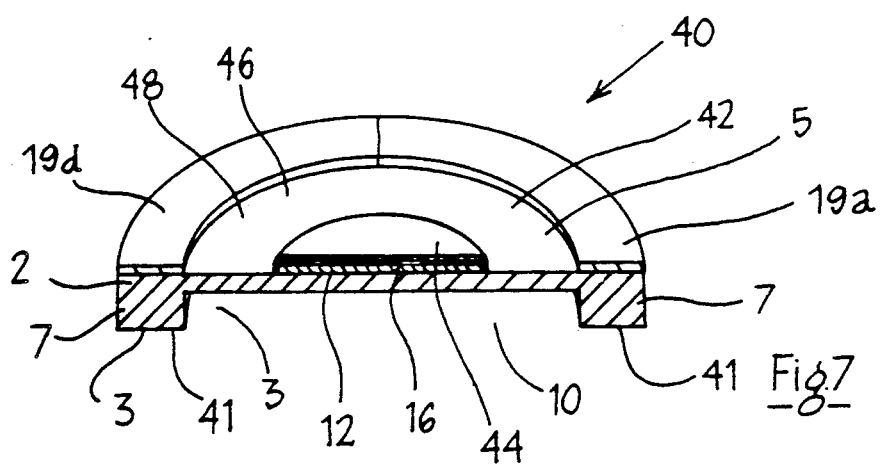
FIG. 7 is a cut-away perspective view of the device of FIG. 6.

Referring now to FIGS. 6 to 8, there is illustrated a device according to a further embodiment of the invention indicated generally by the reference numeral 40 also for monitoring the quantity of UV radiation received by the skin. The device 40 is somewhat similar to the device 1 and similar components are identified by the same reference numerals. In this case, the housing 2 is of a transparent polymer material, namely polyethylenevinyl acetate copolymer which permits the passage of UV radiation therethrough. The housing 2 comprises a circular top wall 5 with a side wall 7 extending downwardly therefrom. In this embodiment of the invention, the flange 9 has been dispensed with and the pressure sensitive adhesive (not shown) is provided on a face 41 of the side wall 7. The reference patches 19a to 19d are provided around the top wall 5 adjacent the side wall 7. In this embodiment of the invention, the patch 16 of UV sensitive material 12 is provided on an outer support surface 42 of the top wall 5 substantially centrally thereof.

Filter means comprising a cover 44 of transparent polyvinyl chloride similar to the material of the housing 2 of the device 1 extends over the patch 16 for filtering out UV radiation and acting as a barrier to direct UV radiation of wavelength in the range of 280 nanometers to 320 nanometers. The cover 44 being transparent permits visual inspection of the patch 16. Since the housing 2 of the device 40 is of polyethylene vinyl acetate copolymer which permits the passage of UV radiation therethrough, an annular window portion 46 extending around the cover 44 between the cover 44 and the side wall 7 acts as a window means for permitting UV radiation including UV radiation of wavelength in the range of 280 nanometers to 320 nanometers to pass through to the skin in the area of the open mouth 10. Furthermore, reflected UV radiation from the skin passes through the top wall 5 and in turn is absorbed by the patch 16.

The outer surface 48 of the annular window 46 is slightly roughened to form a screen receiving surface for receiving a UV barrier cream or oil, lotion or other such sunscreen material. Accordingly, in use the surface 48 of the device 40 may be coated with the same sunscreen cream, oil or lotion which is being applied to the individual's skin so that the patch 16 is subjected to the same effects of the sunscreen cream to which the individual's skin is being subjected.

In use, the device 40 is attached to the skin of an individual by the pressure adhesive (not shown) on the face 41 of the side wall 7 in similar fashion as the device 1 is attached to an individual's skin. Operation of the device 40 is substantially similar to the device 1 with the exception that where an individual applies a UV barrier oil, cream or lotion to the skin, the same UV barrier oil is applied to the surface 48 of the annular window 46. Accordingly, the device 40 is thus subjected to the same effects of the UV barrier cream as the skin of the individual. It has been found in practice that the application of a sunscreen oil, cream or lotion reduces the amount of UV radiation reaching the skin, and accordingly, it is important to compensate for this effect in the device 40.

Referring now to FIG. 9, there is illustrated a device according to the invention indicated generally by the reference numeral 50 for monitoring the quantity of UV radiation received by the skin of an individual. The device 50 is substantially similar to the device 40 just described with reference to FIGS. 6 to 8 and similar components are identified by the same reference numerals. The main difference between the device 50 and the device 40 is that a closure plate member 51 of material similar to the housing 2, namely, polyethylene vinyl acetate copolymer, is sealably secured to the face 41 of the side wall 7 and extends across the open mouth, thus sealably closing the interior region 3. Accordingly, the interior region 3 is maintained dry. The pressure sensitive adhesive for securing the device 50 to the skin of an individual is provided on an outer face 52 of the plate 51.

Use of the device 50 is identical to that of the device 40. In this case, UV radiation passes through the annular window 46, and in turn through the plate 51 to the skin of the individual. The UV radiation reflected from the skin of the individual falls onto and is collected by the patch 16.

Referring now to FIGS. 10 and 11 there is illustrated a device according to a further embodiment of the invention indicated generally by the reference numeral 60 for monitoring the quantity of UV radiation received by the skin of an individual. The device 60 is somewhat similar to the device 40 described with reference to FIGS. 6 to 7 and similar components are identified by the same reference numeral. The main difference between this device 60 and the device 40 is that instead of the housing 2 being formed by a top wall and side wall, the housing 2 is formed by a solid circular plate member 61 of polyethylene vinyl acetate copolymer. The patch 16 is provided on an outer support surface 62 of the plate member 61. Accordingly, the plate member 61 maintains the patch 16 spaced apart from the skin. The pressure sensitive adhesive is provided on a face 63 of the plate member 61. Use of the device 60 is substantially similar to the device 40. The device 60 is attached to the skin of the individual with the face 63 of the housing 2 abutting against the skin of the individual, thereby securing the device 60 to the skin by means of the pressure sensitive adhesive. UV radiation passes through the annular window 46 and falls on the skin. Reflected UV radiation from the skin passes through the plate member 61 and falls on and is absorbed by the patch 16.

While a particular irreversible UV sensitive material has been described for use in the devices according to the invention described with reference to FIGS. 1 to 11, it is envisaged that other suitable irreversible UV sensitive materials may be used. For example, the irreversible UV sensitive material may be selected from any one or more of the following groups:

oxazolidine-dione compounds such as the type disclosed in U.S. Pat. No. 3,903,423, xanthenone compounds of the type disclosed in U.S. Pat. No. 3,903,423, tetrazolium salts of the type disclosed in U.S. Pat. No. 3,449,572, 2(2'4' dinitrobenzyl)pyridine referred to in U.S. Pat. No. 3,194,963 photosensitive onium salts in the presence of a dyestuff which changes colour when protonated of the type disclosed in European Patent Specification No. 0,125,102, and any other photosensitive system that can be used to produce a colour or a colour change.

Needless to say, other irreversible UV sensitive materials may be used. Since some of the above irreversible UV sensitive materials have been found to absorb UV radiation of wavelengths outside the range of 280 nanometers to 400 nanometers, it may in certain cases be necessary to tune the frequency absorption to the wavelength range of 280 nanometers to 400 nanometers. This may be done by placing a layer of suitable screening material over the patch of irreversible UV sensitive material so that screening material would act as a barrier to all radiation other than UV radiation of wavelength in the range of 280 to 400 nanometers. It is believed that suitable screening materials are parsol (Givaudan) and Uvinal (BASF) contained in a suitable binder. It will also of course be appreciated that while the UV sensitive material has been described as changing colour on being subjected to UV radiation, any other characteristic of the material may change besides colour. For example, in certain cases, it is envisaged that the shade of the colour, in other words, the optical density of the colour of the UV sensitive material may change, and needless to say, other characteristics besides colour may change. Once such characterisitics can be easily measured and compared against reference characteristics, a material with such a characterisitic would be adequate for use with the device according to the invention. By manipulation of the concentration of selected UV colouring material and with the appropriate use of light absorbing chemicals to form a filter, then in combination with suitable geometry, the device acts as a quantitative measure of UVB radiation. We have found that there is a direct relationship between the tolerance to UVB radiation of the skin and the quantity of UVB radiation reflected. Accordingly, the amount of UV radiation available to bring about a change in the shade of colour of the patch is a direct measure of the tolerance of that particular skin to the harmful UVB radiation. The amount of UVB radiation reflected is not just dependent upon the character of the skin but also depends upon the amount incident upon the skin, that is the surface area of the window means. The amount of UVB reflected from the skin varies from 20% for a dark sun-tanned person to 45% for a fresh-complexioned light-skinned person. The amount, therefore, which is incident upon the UV sensitive material may be calculated from simple geometry knowing the size and shape of the window means, the size and shape of the patch of UV sensitive material and the height of the UV sensitive material from the skin. The preferred height is between 1 and 10 mm.

Studies (Pathak) have shown that the MED for a fair-skinned sensitive person (skin type 1) is equivalent to a UVB energy of 20 mJcm$^{-2}$. Therefore, the optical density (O.D.) of the UV sensitive material after UV radiation of this level has been received is chosen as the reference O.D. to enable the device to record the receipt of 1 MED. The O.D. colour change chosen for other skin types might be the same or might be different. O.D.'s (reflectance) in the range of 0.2 to 2.0 have been found to be satisfactory for this purpose. The amounts of UV energy tolerated by other types would be higher than that for skin type 1, for example 1.5, 2.0., 3.0, 4.0, etc. times 20 mJc$^{-2}$. Thus, the device could be used in a quantitative way to record the tolerance of other skin types by a change in O.D. of the photosensitive layer to that of the appropriate reference after the receipt of the appropriate amount of energy.

It will also be appreciated that while particular shapes and constructions of the devices have been described, any other suitable shape or construction could be used.

Furthermore, it will be appreciated that any other support means may be used besides that described. It will also of course be appreciated that where the support means is formed by a top wall in a housing, the housing may be of any other shape or construction.

Further, it has been found that where a protective means for example a protective layer similar to the protective layer 31 of the device 30 is used, it provides a threshold effect, in other words, the patch of irreversible UV sensitive material does not commence to change colour or shade until the protective layer has been fully decomposed. It is envisaged in certain cases that the protective means may be provided by a material similar to that of the protective layer, which may be impregnated with the UV sensitive material. Indeed, any other suitable material which breaks down quickly on being exposed to UV radiation may be used as the protective means.

It will also of course be appreciated that other suitable filter means for preventing the patch of UV sensitive material from receiving direct UV radiation from the sun or other source of UV radiation could be used. Further, it will be appreciated that filter means of other materials may be used. In certain cases, the filter means may be dispensed with. Furthermore, while the filter means has been described as acting as a barrier to UV radiation of wavelength in the range of 280 to 320 nanometers, it is believed that the filter means may be provided to act as a barrier to UV radiation of a broader wavelength range, for example, it is envisaged that the filter means may act as a barrier to UV radiation of wavelength in the range of 260 nanometers to 340 nanometers, and in other cases the filter means may act as a barrier to UV radiation of wavelength in the range of 260 nanometers to 400 nanometers. Indeed, in certain cases, it is envisaged that the filter means may act as a barrier to all UV radiation.

It is also envisaged that in the embodiment of the invention described with reference to FIGS. 1 to 4, instead of the housing forming the filter means, it is envisaged that a filter means provided by a disc mounted between the support surface of the top wall and the patch of UV sensitive material may be provided. For example, in such a case, it is envisaged that the filter means may be provided by a disc mounted on the support surface and the patch of UV sensitive material would be applied to the filter disc.

It will also be appreciated that other window means for allowing UV radiation to the skin could be used other than the window means described. While in the embodiment of the invention described with reference to FIGS. 1 to 4 the ratio of the total area of the window means to the area of the top wall has been described as being 50%, it is believed that good results would be obtained with a ratio of total window area to the area of the top wall in the range of 30% to 70% and adequate results would be achieved with a ratio of total window area to the area of the top wall in the range of 20% to 80%.

It will of course be appreciated that while the devices have been described as comprising four reference patches, any number of reference patches could be provided. Indeed, in certain cases, it is envisaged that a single reference patch may be provided, or indeed, a single reference colour shade may be provided entirely around the flange. In which case, a person would use a device with a reference colour shade suitable for his/her skin type. Indeed, it has been found that the UV reflectances of different skins vary by a factor of more than two, and it is therefore clear that the device may be used without a precise knowledge of the user's skin type. This reduces the required number of reference shades needed to cover the spectrum of tolerances.

While the housing has been described as being of polyvinyl chloride, it will be appreciated that it could be of any other suitable material, whether stabilised or unstabilised. Typical examples would be polyurethanes, silicones and the like which may or may not, but in general, preferably, would be stabilised against UV degradation.

Further, while the height of the side wall from the support surface of the top wall has been described as being 3 mm, and accordingly, the UV radiation sensitive material has been described as being spaced apart a distance of 3 mm from the individual's skin, the UV sensitive material may be spaced apart from the skin other distances without adverse effects. Indeed, in certain cases, it is envisaged that the UV sensitive material may be spaced apart a distance as low as 1 mm from the skin and even less, while in other cases, the UV sensitive material may be spaced apart a distance up to 10 mm, and even greater distances without adverse effects.

While the UV sensitive material has been described as being provided as a patch mounted centrally on the top wall of the housing, the patch of UV sensitive material may be provided in any other suitable location. Indeed, it is envisaged that the patch may be provided by an annular ring which would extend around a window opening. Further, while the UV sensitive material has been described as being provided as a patch, it may be proivded by any other suitable means. Needless to say, if desired, the UV sensitive material may be mounted on the inner or outer surfaces the housing.

We claim:

1. A device for monitoring the quantity of UV radiation received by the skin, the device comprising
a support means defining a support surface,
a substantially irreversible UV sensitive material on the support surface, the UV sensitive material having a characteristic which alters substantially irreversibly on being subjected to UV radiation,
securing means for attaching the support means to the skin, said support means supporting said UV sensitive material such that at least a portion of the UV sensitive material is spaced apart from the skin to receive reflected UV radiation from the skin.

2. A device as claimed in claim 1 in which filter means is provided to prevent at least some UV radiation direct from the UV radiation source falling on the UV sensitive material.

3. A device as claimed in claim 2 in which the filter means acts as a barrier to UV radiation of wavelength in the range of 260 nanometers to 400 nanometers.

4. A device as claimed in claim 3 in which the filter means acts as a barrier to UV radiation of wavelength in the range of 260 nanometers to 340 nanometers.

5. A device as claimed in claim 2 in which the filter means is transparent to allow the UV sensitive material to be viewed therethrough.

6. A device as claimed in claim 2 in which the support member forms the filter means.

7. A device as claimed in claim 2 in which the filter means comprises a filter disc defining a pair of opposite faces, the filter disc being secured to the support means by one of said opposite faces of the filter disc, and the UV sensitive material being provided on the other of said opposite faces of the filter disc.

8. A device as claimed in claim 1 in which the support means supports the UV sensitive material spaced apart from the skin a distance of at least 1 mm.

9. A device as claimed in claim 1 in which at least one reference characteristic is provided for comparison with the UV sensitive material, the reference characteristic corresponding to the state to which the characteristic of the UV sensitive material would alter after the UV sensitive material had been subjected to a predetermined quantity of UV radiation.

10. A device as claimed in claim 9 in which the reference characteristic is provided in a plurality of different reference states, the reference states corresponding to respective states to which the characteristic of the UV sensitive material would alter after the UV sensitive material had been subjected to respective different predetermined quantities of UV radiation.

11. A device as claimed in claim 9 in which the characteristic of the UV sensitive material which alters is the colour of the UV sensitive material.

12. A device as claimed in claim 1 in which the support means comprises a support member formed by a plate member.

13. A device as claimed in claim 1 in which window means is provided in the support means to permit the passage of UV radiation therethrough to the skin.

14. A device as claimed in claim 13 in which the total area of the window means constitutes in the range of 20% to 80% of the area of the support means.

15. A device as claimed in claim 1 in which the device comprises a housing defining a hollow interior region having an open mouth to the interior region, the support means being formed by a portion of the housing, the UV sensitive material being spaced apart from the open mouth, and the securing means being provided adjacent the open mouth.

16. A device as claimed in claim 1 in which the support means is of material which permits the passage of UV radiation therethrough.

17. A device as claimed in claim 1 in which a surface of the support means defines a screen receiving surface comprising means for receiving a UV barrier cream, oil or other sun screen material.

18. A device as claimed in claim 1 in which the UV sensitive material is selected from any one or more of the following materials:
oxazolidine-dione compounds,
tetrazolium salts,
2(2'4' dinitrobenzyl)pyridine,
photosensitive onium salts in the presence of a dyestuff which changes colour when protonated.

19. A method for monitoring the quantity of UV radiation received by the skin, the method comprising the step of placing an irreversible UV sensitive material adjacent the skin of an individual, the UV sensitive material having a characteristic which alters on being subjected to UV radiation, collecting UV radiation reflected by the skin in the UV sensitive material, observing the UV sensitive material to determine a change in the characteristic in the UV sensitive material for determining the quantity of UV radiation received by the skin.

20. A method as claimed in claim 19 in which the method further comprises the step of comparing the characteristic of the UV sensitive material with a reference characteristic, the reference characteristic corresponding to the state to which the characteristic of the UV sensitive material would alter after the UV sensitive material had been subjected to a predetermined quantity of UV radiation.

* * * * *